(12) United States Patent
Murillo et al.

(10) Patent No.: US 12,350,174 B2
(45) Date of Patent: *Jul. 8, 2025

(54) FIXATION MEMBER INSERTER INSTRUMENT

(71) Applicant: Astura Medical Inc., Irving, TX (US)

(72) Inventors: Fred Murillo, Irving, TX (US); Thomas Purcell, Irving, TX (US)

(73) Assignee: ASTURA MEDICAL INC, Irving, TX (US)

( * ) Notice: Subject to any disclaimer, the term of this patent is extended or adjusted under 35 U.S.C. 154(b) by 54 days.

This patent is subject to a terminal disclaimer.

(21) Appl. No.: 18/373,085

(22) Filed: Sep. 26, 2023

(65) Prior Publication Data

US 2024/0016627 A1 Jan. 18, 2024

Related U.S. Application Data

(63) Continuation of application No. 17/033,636, filed on Sep. 25, 2020, now Pat. No. 11,766,342.

(51) Int. Cl.
*A61F 2/46* (2006.01)
*A61F 2/30* (2006.01)

(52) U.S. Cl.
CPC ........ *A61F 2/4611* (2013.01); *A61F 2/30734* (2013.01); *A61F 2002/30477* (2013.01); *A61F 2002/30604* (2013.01); *A61F 2002/4615* (2013.01); *A61F 2002/4629* (2013.01)

(58) Field of Classification Search
CPC .................................................. A61F 2/4611
See application file for complete search history.

(56) References Cited

U.S. PATENT DOCUMENTS

| | | | |
|---|---|---|---|
| 8,641,766 B2* | 2/2014 | Donner | A61B 17/846 606/279 |
| 9,901,459 B2* | 2/2018 | Faulhaber | A61F 2/4455 |
| 9,980,824 B2* | 5/2018 | Zappacosta | A61F 2/4455 |
| 10,433,975 B2* | 10/2019 | Ashleigh | A61F 2/4611 |
| 10,631,999 B2* | 4/2020 | Gilbride | A61B 17/844 |
| 10,758,370 B2* | 9/2020 | Gilbride | A61B 17/8685 |
| 11,576,785 B1* | 2/2023 | Cummins | A61F 2/4455 |
| 11,672,674 B2* | 6/2023 | Shoshtaev | A61F 2/4611 623/17.16 |
| 2011/0098747 A1* | 4/2011 | Donner | A61B 17/7044 606/264 |

(Continued)

*Primary Examiner* — Matthew J Lawson
(74) *Attorney, Agent, or Firm* — Michael R Shevlin (57) ABSTRACT

A fixation member inserter instrument attaches to an interbody spacer and assists in the insertion of the interbody spacer into the intravertebral spacer. The distal end of the fixation member inserter instrument includes a fixation member guide with two or more fixation members that is configured to simultaneously deliver the two or more fixation members during the fixation member impaction process. The interbody spacer is attached to the inserter instrument by a threaded rod adjacent to the main body of the fixation member inserter instrument. There is an impaction rod extending through the device which connects to the two or more fixation members in the fixation member guide. When the impaction rod is impacted on a proximal end, the distal end contacts the two or more fixation members simultaneously and forces them into the vertebral body at the same time.

18 Claims, 10 Drawing Sheets

(56) References Cited

U.S. PATENT DOCUMENTS

| | | | |
|---|---|---|---|
| 2013/0150968 A1* | 6/2013 | Dinville | A61F 2/46 623/17.16 |
| 2017/0311997 A1* | 11/2017 | Lequette | A61F 2/4611 |
| 2017/0340453 A1* | 11/2017 | Kaufmann | A61F 2/4611 |
| 2018/0256354 A1* | 9/2018 | Tanaka | A61F 2/4611 |
| 2020/0138595 A1* | 5/2020 | Shoshtaev | A61F 2/447 |
| 2023/0248524 A1* | 8/2023 | Bohenick | A61F 2/4455 623/17.11 |

* cited by examiner

FIXATION MEMBER INSERTER INSTRUMENT

CROSS-REFERENCE TO RELATED APPLICATIONS

This application is a continuation of U.S. application Ser. No. 17/033,636, filed Sep. 25, 2020, which claims the benefit of U.S. Provisional Application No. 62/905,385 filed Sep. 25, 2019, which is incorporated herein by reference.

FIELD

The present invention relates generally to the field of surgery, and more specifically, to a fixation member inserter instrument for use with an anterior interbody spacer for attachment of the intervertebral anterior interbody spacer to adjacent vertebrae during anterior spinal fixation surgery.

BACKGROUND

A spinal disc can become damaged as a result of degeneration, dysfunction, disease and/or trauma. Conservative treatment can include non-operative treatment through exercise and/or pain relievers to deal with the pain. Operative treatment options include disc removal and replacement using an interbody spacers such as anterior cervical interbody fusion (ACIF), anterior lumbar interbody fusion (ALIF), direct lateral interbody fusion (DLIF) (also known as XLIF), posterior lumbar interbody fusion (PLIF), and transforaminal lumbar interbody fusion (TLIF).

The spacers are placed in the interdiscal space between adjacent vertebrae of the spine, resulting in spinal fusion of the adjacent vertebra wherein two or more vertebrae are joined together (fused) by way of interbody spacers, sometimes with bone grafting, to form a single bone. The current standard of care for interbody fusion requires surgical removal of all or a portion of the intervertebral disc. After removal of the intervertebral disc, the interbody spacer is inserted in the space between the adjacent vertebrae.

Ideally, the interbody spacer should stabilize the intervertebral space and allow fusion of the adjacent vertebrae. Moreover, during the time it takes for fusion to occur, the interbody spacer body should have sufficient structural integrity to withstand the stress of maintaining the space without substantially degrading or deforming and have sufficient stability to remain securely in place prior to actual bone ingrowth fusion.

Many interbody spacers include a spinal plate that requires a secondary action to install the plate in-situ to inhibit fixation screw migration. The plate typically uses between two and four fasteners to attach the spinal plate to the adjacent vertebrae. This secondary action is time consuming and cumbersome when the surgical procedure is time sensitive.

It would be desirable to provide an improved device to attach a spinal plate to adjacent vertebrae.

SUMMARY

Disclosed is a fixation member inserter instrument with a unique modular fixation member guide that is used to simultaneously deliver multiple fixation members to attach a spinal plate to vertebrae.

A fixation member inserter instrument attaches to an interbody spacer and assists in the insertion of the interbody spacer into the intravertebral spacer. Attached to the distal end of the fixation member inserter instrument is a modular fixation member guide that holds fixation members and guides the fixation members during the impaction process. An interbody spacer may be attached to the inserter by a threaded rod adjacent to the main body of the fixation member inserter instrument. There is an impaction rod extending through the device which connects to the fixation member. When the impaction rod is impacted on a proximal and, the distal end contacts the fixation members and forces them into the vertebral body.

DETAILED DESCRIPTION

The invention is directed to a fixation member inserter instrument that is designed to attach an interbody spacer to spinal vertebrae. During anterior spinal fixation surgery an intervertebral disc is removed and an interbody spacer inserted into the space between the adjacent vertebrae. The interbody spacer typically includes a spinal plate having fastener holes. After placement of the interbody spacer, fixation members are inserted through the fastener holes and attached to the adjacent vertebrae above and below the interbody spacer with the fixation member inserter instrument. In some embodiments, the fixation member inserter instrument is also an implant inserter instrument.

Figure 1:
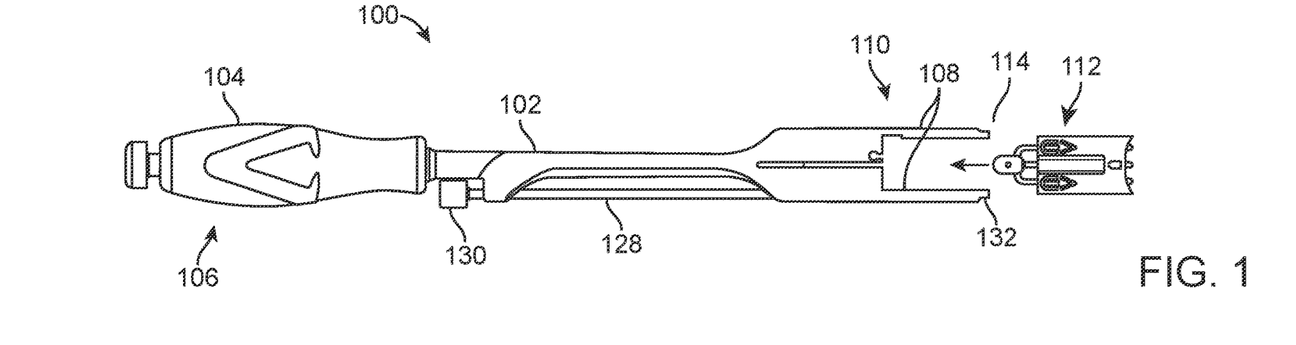
FIGS. 1 and 2 shows one embodiment of a fixation member inserter instrument with modular/interchangeable fixation member guide for use with different interbody spacers.
Figures 2, 3:
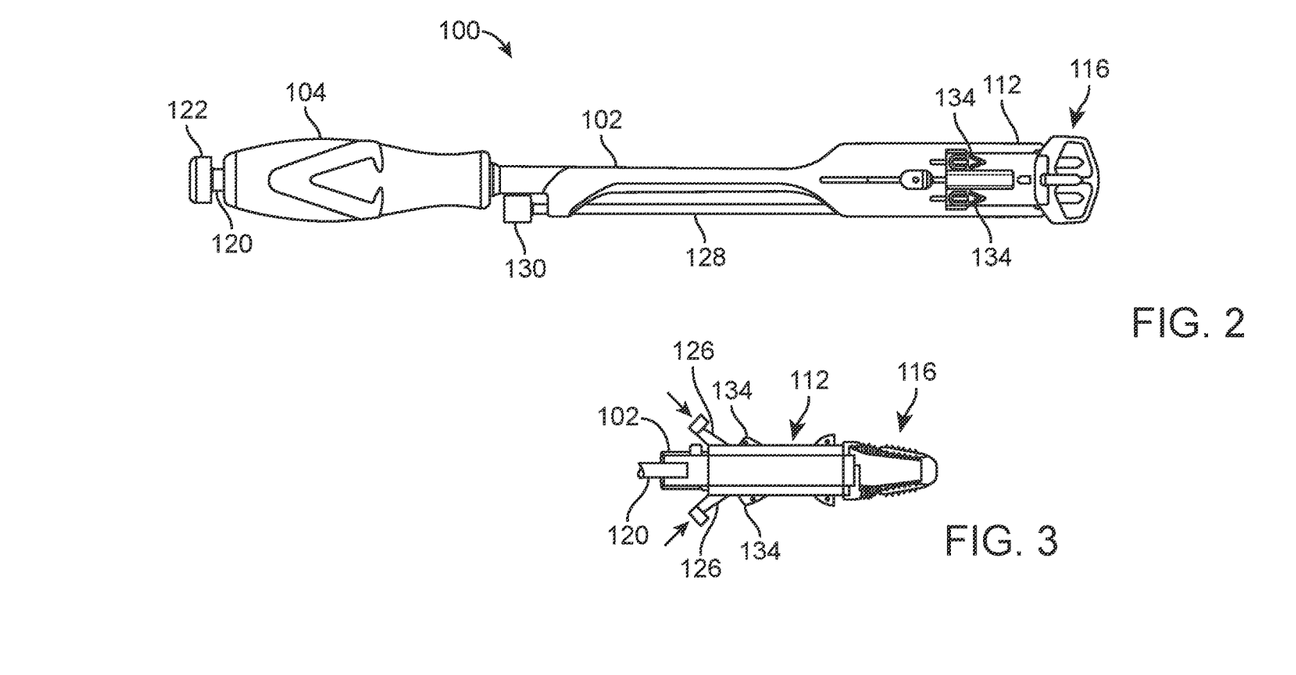
FIG. 3 shows a side view of the distal end of the fixation member inserter instrument and fixation member guide.

FIGS. 1 and 2 show one embodiment of a fixation member inserter instrument 100 including a main body 102 having a handle portion 104 on a proximal end 106 and fixation member guide attachment arms 108 extending distally from a distal end 110 configured to couple with a modular/interchangeable fixation member guide 112. One or more protrusions 114 are positioned on the distal end to engage an interbody implant 116.

The main body 102 further includes a cannula 118 extending from the proximal end 106 to the distal end 110. The cannula 118 being sized to slidably receive an impaction rod 120 having an impaction head 122 on the proximal end and a fixation member impact end 124 on a distal end. The impaction head 122 is designed to receive an impact force and transfer the force to fixation member impact end 124.

The modular fixation member guide 112 is designed as an integrated, pre-assemble fixation member guide to hold two or more fixation members 126, the number of fixation members depending on the various plates used for the interbody spacer 116. In some embodiments, the modular fixation member guide 112 includes two fixation members for an interbody spacer with a zero height plate. In some embodiments, the modular fixation member guide 112 includes three fixation members for an interbody spacer with a half-height plate. In some embodiments, the modular fixation member guide 112 includes four fixation members for an interbody spacer with a full-height plate.

The fixation members serve as the fixation members which attach the interbody spacer to the vertebrae. In some embodiments the fixation member sizes are 5.5 mm in diameter and 15-30 mm in length. The fixation members have a pointed tip on a distal end to allow them to pierce the endplates as they are impacted into the vertebral endplates. The head of the fixation member has a triangular shape which serves as an alignment feature during insertion through the inserter. The head of the fixation member may also include a female thread which serves as an attachment feature for removal.

The modular fixation member guide 112 is designed to deliver all of the fixation members with a single impact on the impaction head 122.

The fixation member inserter instrument 100 further includes a threaded rod 128 adjacent to the main body 102 with a proximal handle 130 and a threaded distal end 132 designed to hold an interbody spacer 116.

The fixation members may be any type suitable for plate attachment to the vertebrae, for example, nails, screws, pins, tacks, brads, spikes, cleats, or other suitable fixation members. In the embodiments shown below, the fixation members 126 are shown as nails.

FIG. 3 is a side view of the distal end of the fixation member inserter instrument 100 and fixation member guide 112 showing the loading of nails 126 through holes 134 into the top and bottom of the fixation member guide 112 into a curved delivery portal 136. In some embodiments the fixation member guide is a modular fixation member guide. On other embodiments, the fixation member guide may be part of the fixation member inserter instrument.

Figure 4:
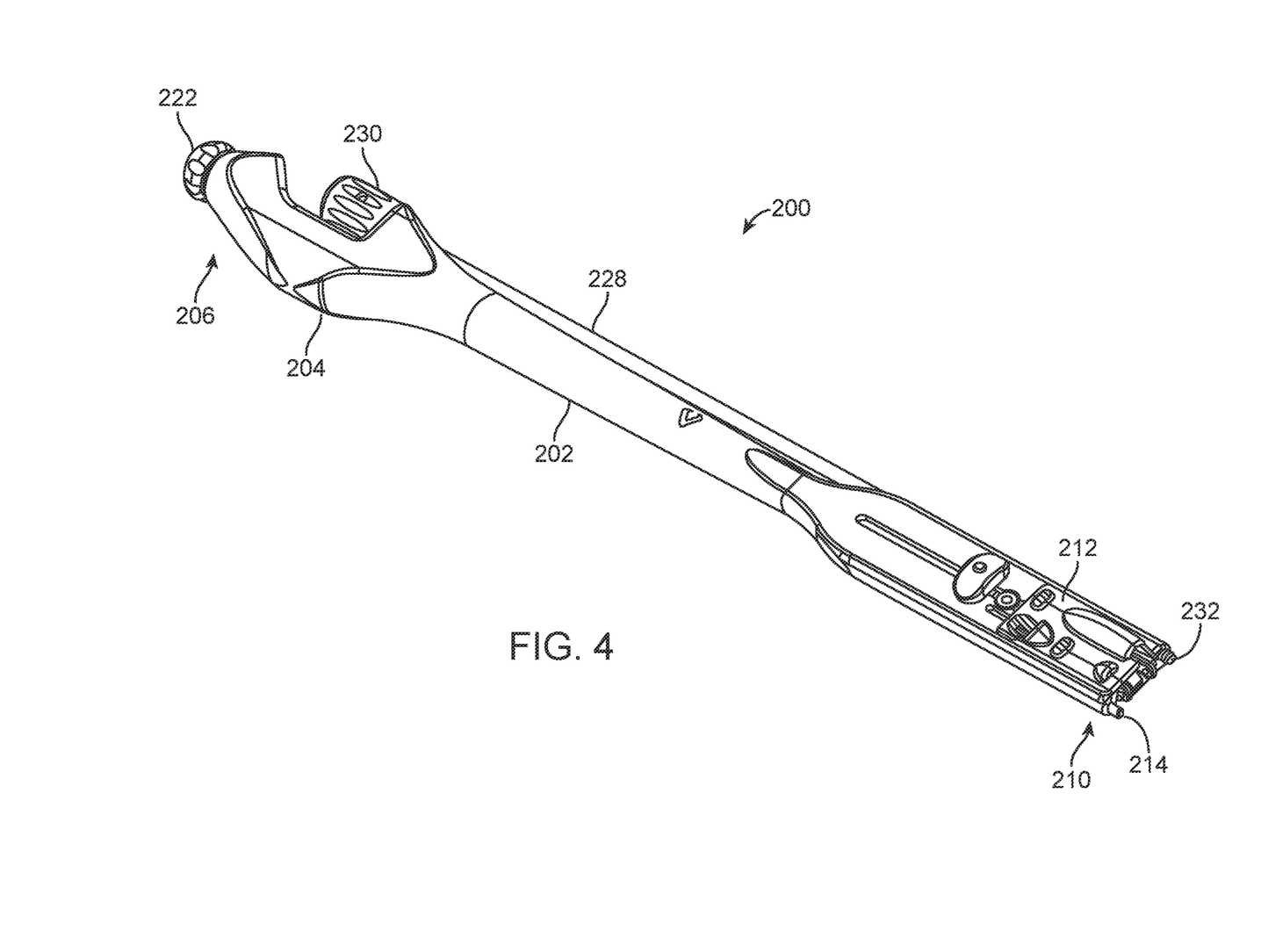
FIG. 4 shows another embodiment of a fixation member inserter instrument having a fixation member guide holding two fixation members coupled with an interbody spacer.

FIG. 4 shows another embodiment of a fixation member inserter instrument 200 having a fixation member guide 212 holding two nails 226 to use with an interbody spacer 216. The fixation member inserter instrument 200 may be used with a cervical interbody. The nails 126 are deployed from the distal end of the fixation member guide 212 into the interbody spacer 216. The fixation member inserter instrument 200 includes a main body 202 having a handle portion 204 on a proximal end 206 and a distal end 210 configured to couple with a fixation member guide 212. One or more protrusions 214 are also positioned on the distal end to engage an interbody implant 216.

The main body 202 further includes a cannula 218 extending from the proximal end 206 and the distal end 210. The cannula 218 being sized to slidably receive an impaction rod 220 having an impaction head 222 on the proximal end and a distal fixation member impact end 224. The impaction head 222 is designed to receive an impact force and transfer the force to fixation member impact end 224. The fixation member guide 212 is designed to simultaneously deliver the two nails 226 with a single impact on the impaction head 222.

The fixation member inserter instrument 200 further includes a threaded rod 228 adjacent to the main body 202 with a proximal handle 230 and a threaded distal end 232 designed to hold an interbody spacer 216.

Figure 5A:
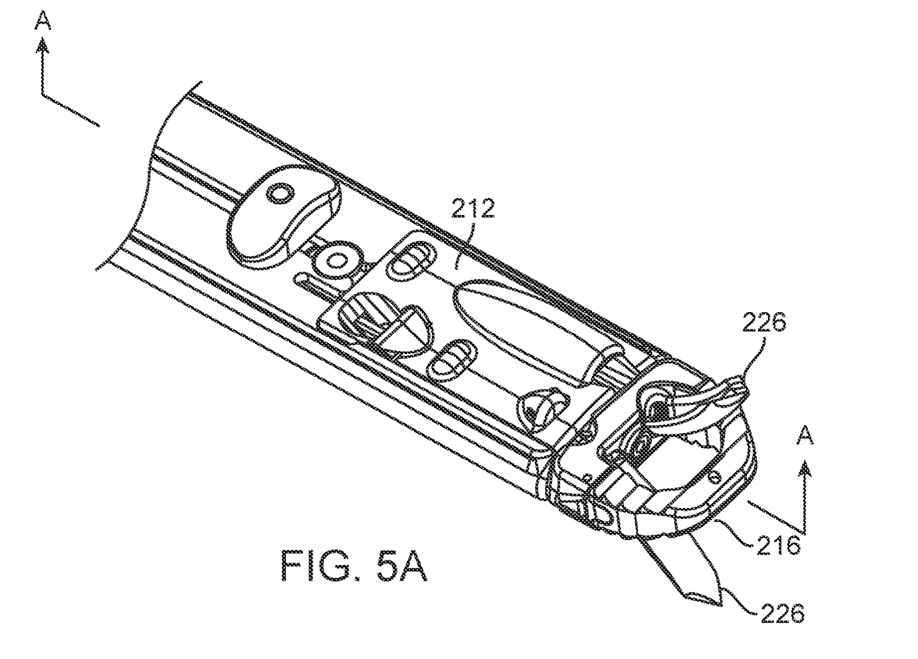
FIGS. 5A and 5B show the distal end of the fixation member inserter instrument and a sectional view at B-B.
Figure 5B:
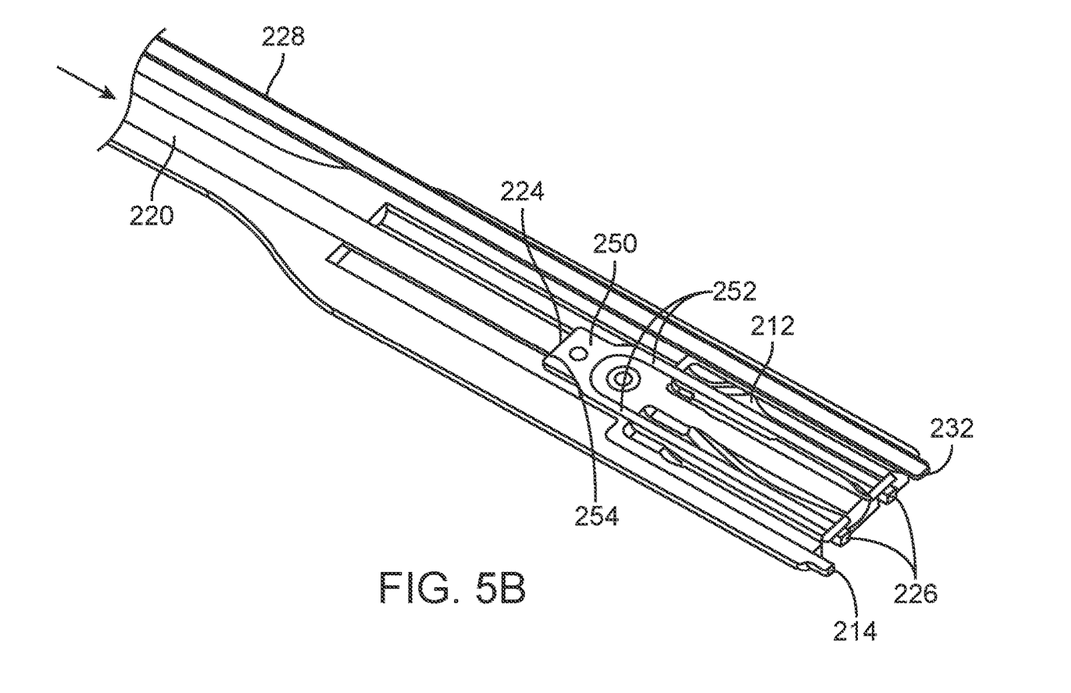

FIGS. 5A and 5B show the distal end of the fixation member inserter instrument 200 and a sectional view at A-A. The fixation member inserter instrument 200 is configured to hold two nails 226 for use with an interbody spacer 216. One nail 226 is configured to couple to a spinal vertebrae above the interbody spacer 216 and the second nail 226 is configured to couple to a spinal vertebrae below the interbody spacer 216.

Sectional view at A-A shows the internal components of the fixation member guide 212 including a fixation member guide deployment rod 250 with two fixation member deployment prongs 252 to push the two nails 226. The fixation member impact end 224 of the impaction rod 220 contacts a proximal impaction end 254 of the fixation member guide deployment rod 250 and is configured to push the two fixation member deployment prongs 252 from a proximal position to a distal position to simultaneously deploy the two nails 226.

Figure 6:
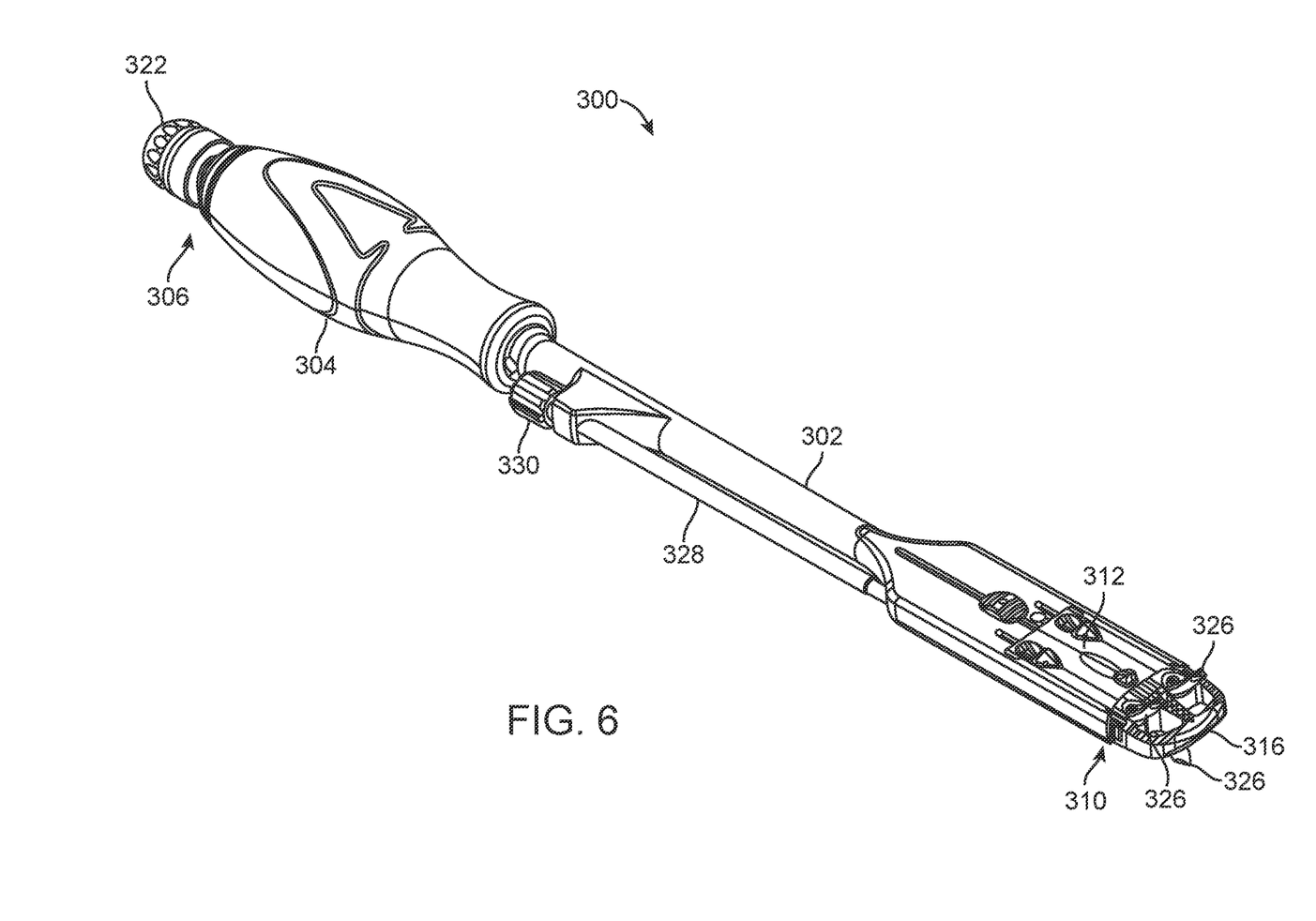
FIG. 6 shows another embodiment of a fixation member inserter instrument having a fixation member guide holding three fixation members coupled with an interbody spacer.

FIG. 6 shows another embodiment of a fixation member inserter instrument 300 having a fixation member guide 312 holding three nails 326 coupled with an interbody spacer 316. The nails 326 shown are deployed from the distal end of the fixation member guide 312 and into the interbody spacer 316. The fixation member inserter instrument 300 includes a main body 302 having a handle portion 304 on a proximal end 306 and a distal end 310 configured to couple with a fixation member guide 312. One or more protrusions 314 are also positioned on the distal end to engage an interbody implant 316.

The main body 302 further includes a cannula 318 extending from the proximal end 306 and the distal end 310. The cannula 318 being sized to slidably receive an impaction rod 320 having an impaction head 322 on the proximal end and a distal fixation member impact end 324. The impaction head 322 is designed to receive an impact force and transfer the force to fixation member impact end 324. The fixation member guide 312 is designed to simultaneously deliver the three nails 326 with a single impact on the impaction head 322.

The fixation member inserter instrument 300 further includes a threaded rod 328 adjacent to the main body 302 with a proximal handle 330 and a threaded distal end 332 designed to hold an interbody spacer 316.

Figure 7A:
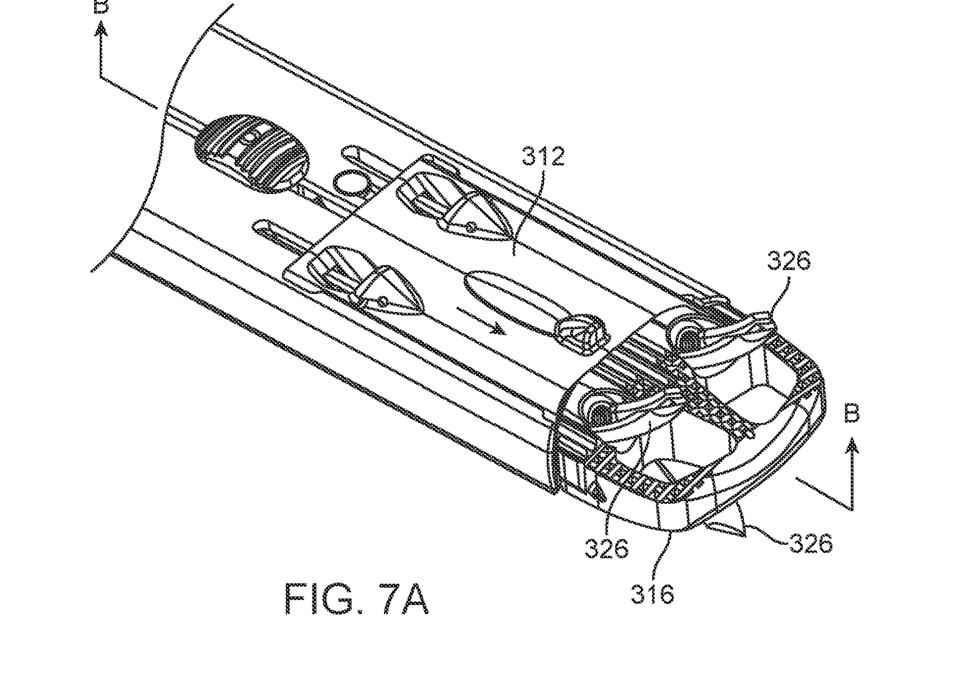
FIGS. 7A and 7B show the distal end of the fixation member inserter instrument and a sectional view at B-B.
Figure 7B:
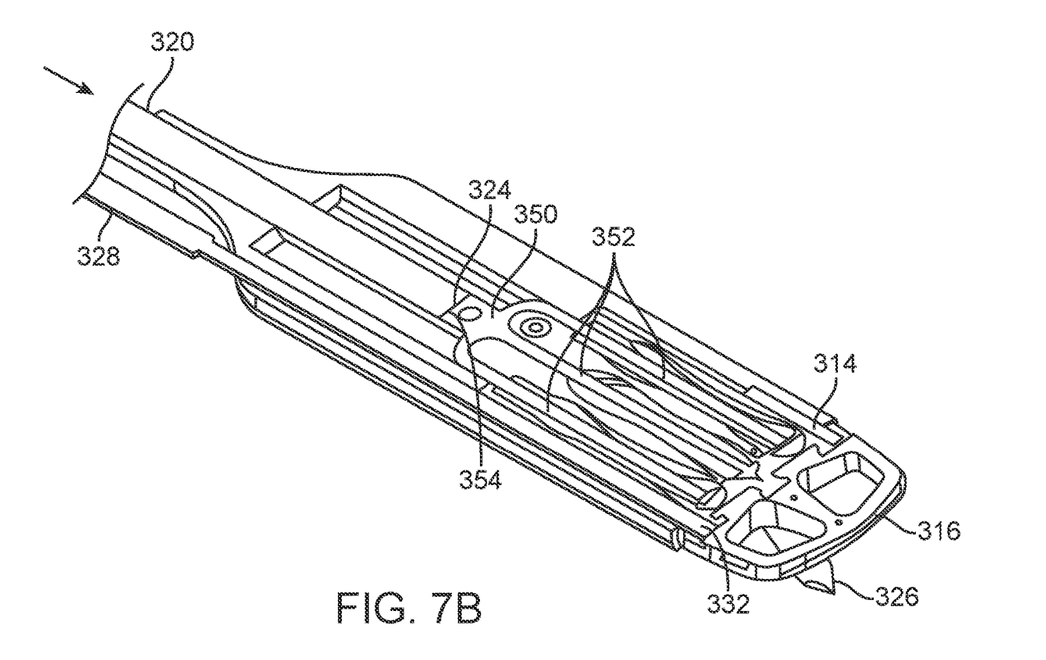

FIGS. 7A and 7B show the distal end of the fixation member inserter instrument 300 and a sectional view at B-B. The fixation member inserter instrument 300 is configured to hold three nails 326 for use with an interbody spacer 316. Two of the nails 326 are configured to couple to a spinal vertebra above the interbody spacer 316 and the third nail 326 is configured to couple to a spinal vertebrae below the interbody spacer 300.

Sectional view at B-B shows the internal components of the fixation member guide 312 including a fixation member guide deployment rod 350 with three fixation member deployment prongs 352 to push the three nails 326. The fixation member impact end 324 of the impaction rod 320 is contacts a proximal impaction end 354 of the fixation member guide deployment rod 350 is configured to push the three fixation member deployment prongs 352 from a proximal position to a distal position to deploy the nails 326 at the same time.

Figure 8A:
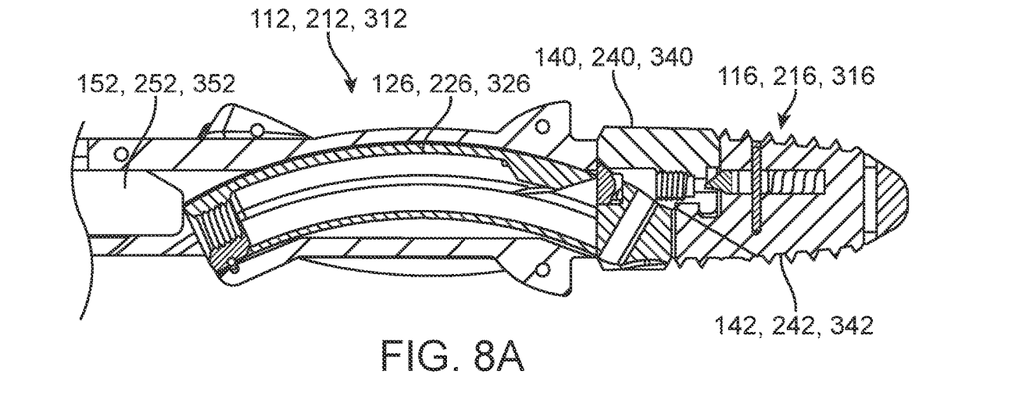
FIGS. 8A, 8B and 8C are cross-sectional side views of the fixation member inserter instrument and fixation member guide showing the delivery of the fixation members.
Figure 8B:
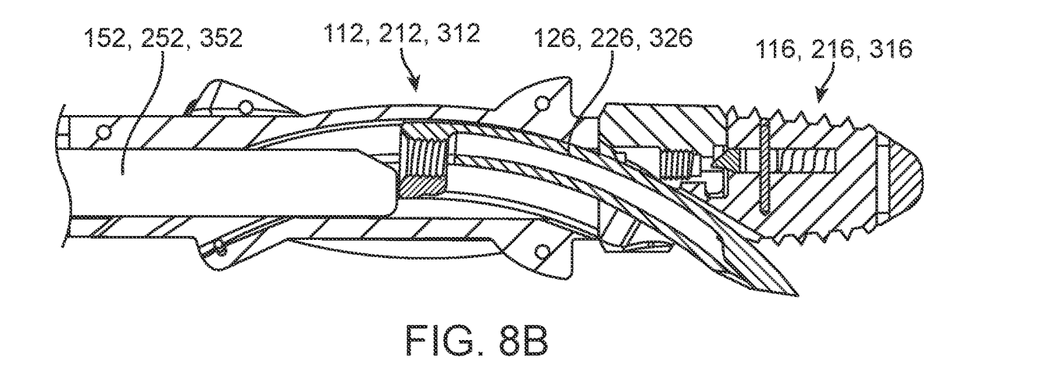
Figure 8C:
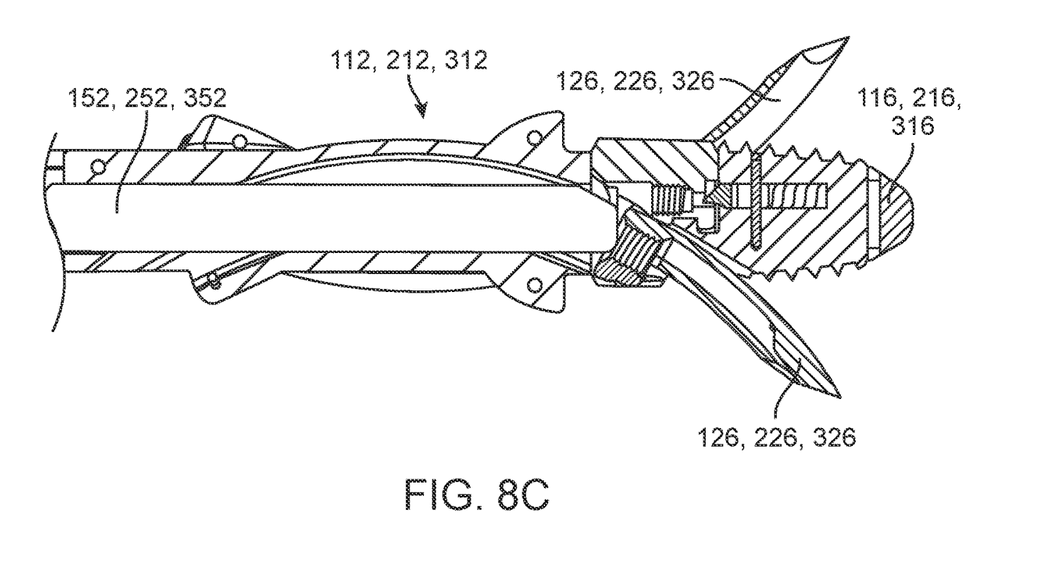

FIGS. 8A-8C are cross-sectional side views of the fixation member inserter instrument 100, 200, 300 and fixation member guide 112, 212, 312 showing the delivery of the nails 126, 226, 326. The fixation member deployment prongs 152, 252, 352 are in contact with the nails 126, 226, 326. In the embodiment shown, the interbody spacer 116, 216, 316 includes a plate 140, 240, 340 coupled with a spacer body 142, 242, 342. The plate 140, 240, 340 is configured to receive the nails 126, 226, 326 and allow them to pass through openings and pierce the vertebrae.

FIG. 8A shows the nails 126, 226, 326 positioned in curved delivery portals 136, 236, 336 of the fixation member guide 112, 212, 312. The fixation member guide 112, 212, 312 includes multiple curved portals 136, 236, 336 in both curved-up or curved-down positions, so that the nails 126, 226, 326 are deployed into vertebrae above and below the interbody spacer 128. The position of the nails 126, 226, 326 in FIG. 8A is how they would be stored within the fixation member guide 112, 212, 312 during the delivery of the interbody spacer 116, 216, 316 to the vertebral space.

Once the interbody spacer 116, 216, 316 is positioned in the desired vertebral space, a force 144, 244, 344 is applied to impaction head 122, 222, 322 of the impaction rod 120. 220. 230, shown in FIG. 8B. The movement of the impaction rod 120, 220, 320 pushes fixation member deployment prongs 152, 252, 352 against the nails 126, 226, 326 and the nails 126, 226, 326 are pushed distally through the interbody spacer 116, 216, 316 and into the vertebrae.

FIG. 8C shows the nails 126, 226, 326 fully deployed from the fixation member guide 112, 212, 312. The nails 126, 226, 326 are deployed in both the upward and downward direction.

Figure 9A:
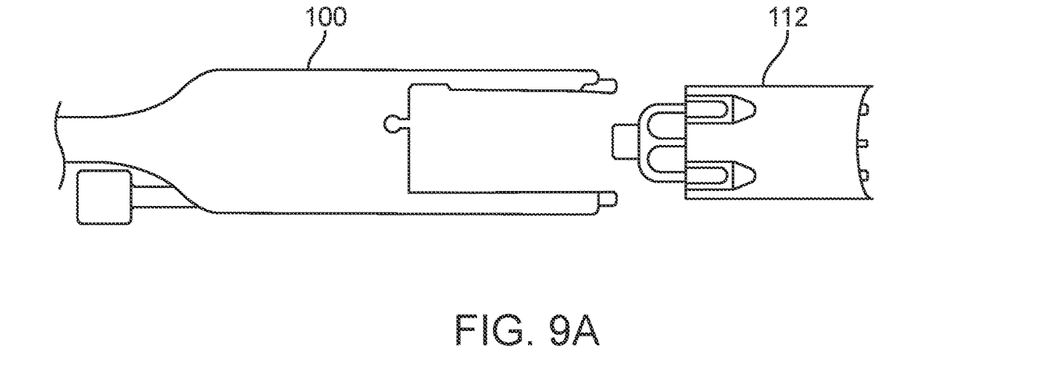
FIGS. 9A-9C show embodiments of a modular fixation member guide for use with fixation member inserter instrument.
Figure 9B:
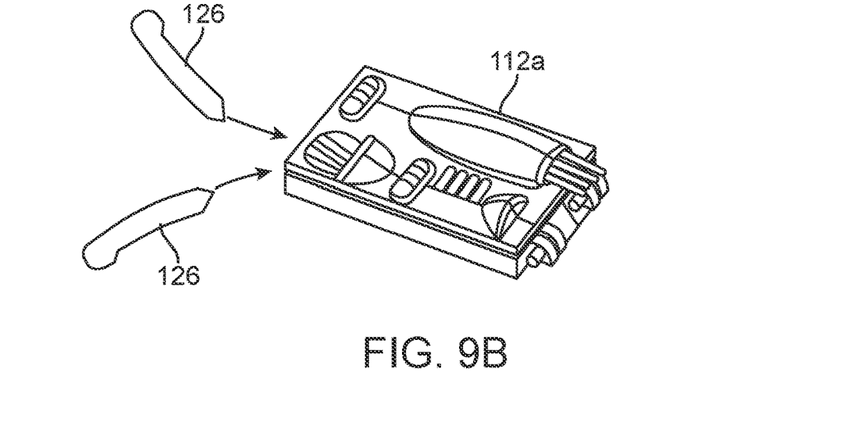
Figure 9C:
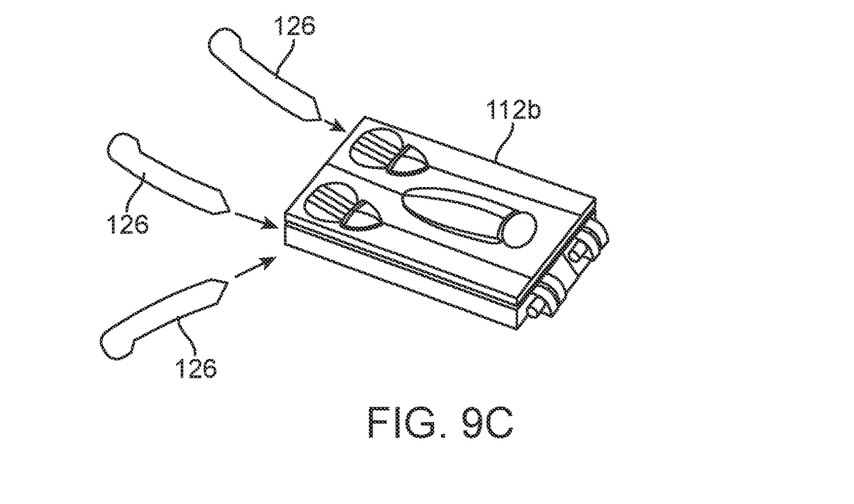

FIGS. 9A-9C show embodiments of a modular fixation member guide 112 for use with fixation member inserter instrument 100. In some embodiments, modular fixation member guide 112 may be preloaded with the fixation members 126 prior to attachment to the main body 102. There may be different configurations of fixation member guides 112 that hold different amounts of nails 126, depending on the plate 140 being used. For example, the fixation member guide 112a may be preloaded with two nails, the fixation member guide 112b may be preloaded with three nails, four nails or more.

Figure 10A:
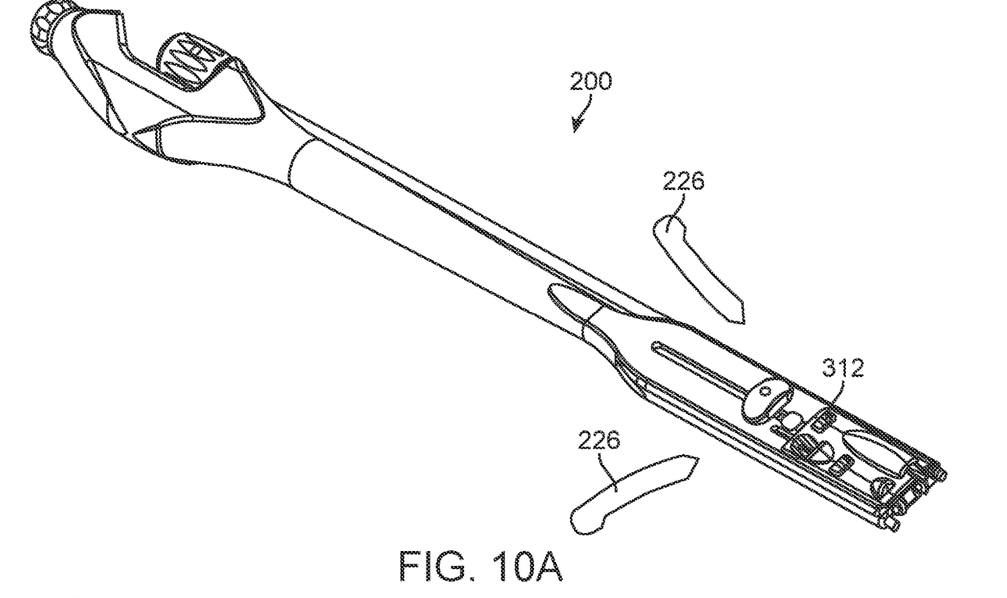
FIGS. 10A and 10B show different embodiments of a fixation member inserter instrument having a fixation member guide being loaded with fixation members.
Figure 10B:
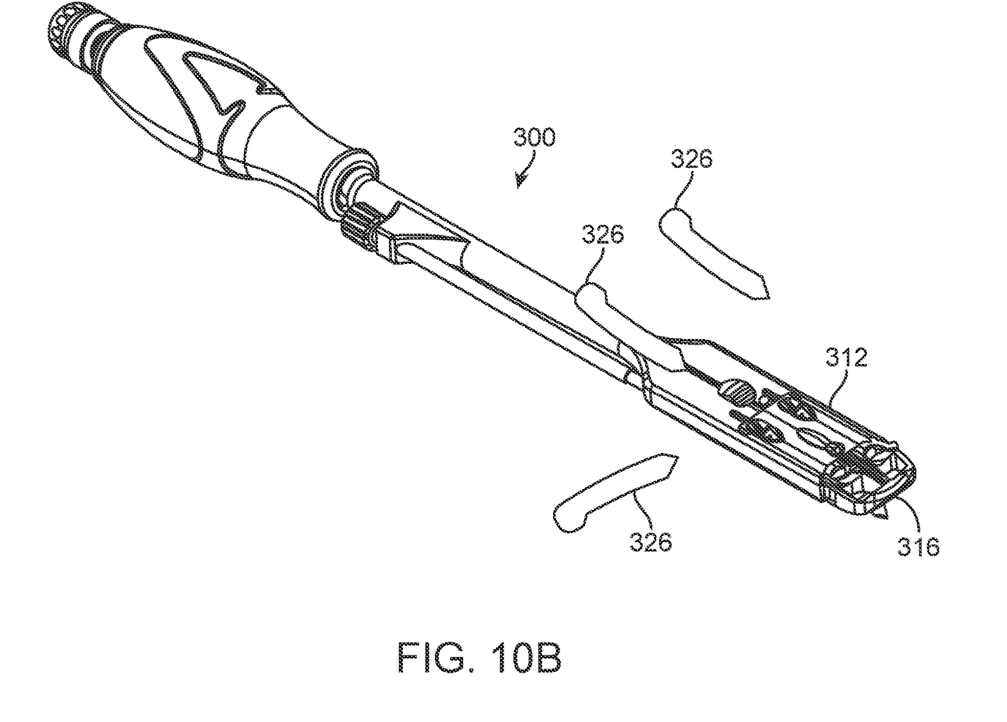

FIGS. 10A and 10B show different embodiments of a fixation member inserter instrument 200, 300 having a fixation member guide 212, 312 being loaded with the nails 226, 326. There may be different configurations of fixation member inserter instruments 200, 300 that are made with different amounts of nails 226, 326, depending on the plate 240, 340 being used. For example, the fixation member guide 212 of fixation member inserter instrument 200 may hold two nails 226 (FIG. 10A) and the fixation member guide 312 of fixation member inserter instrument 300 may hold three nails 326 (FIG. 10B). In other embodiments, a fixation member inserter instrument may hold more than three nails, such as four nails, five nails and so on, depending on the plate 240, 340 being used.

Figures 11A, 11B:
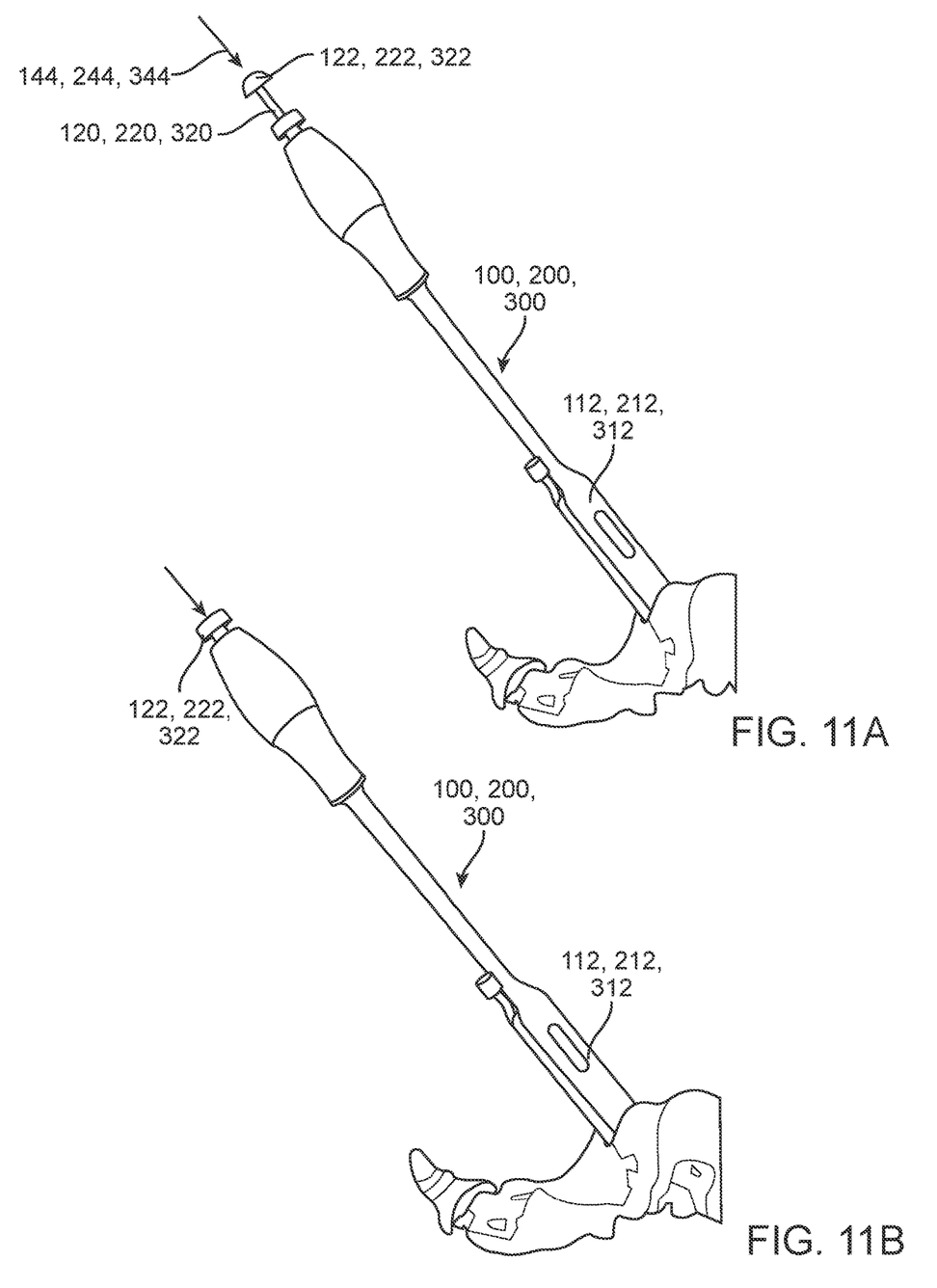
FIGS. 11A and 11B show the fixation member inserter instrument delivering an interbody implant.

FIGS. 11A and 11B show the fixation member inserter instrument 100, 200, 300 delivering an interbody implant. The fixation member inserter instrument 100, 200, 300 attaches to the interbody spacer 116. 216, 316 and assists in the insertion of the interbody spacer into the intravertebral space. The interbody spacer 116, 216, 316 is attached to the fixation member inserter instrument 100, 200, 300 by the threaded rod 128, 228, 328. The fixation member guides 112, 212, 312 are at the distal end of the fixation member inserter instrument 100, 200, 300 proximate the intravertebral space. There is an impaction rod 120, 220, 320 coupled to the fixation member guides 112, 212, 312. When the impaction rod 120, 220, 320 is impacted 144, 244, 344 it forces the nails 126, 226, 326 into the vertebral body 160 The fixation member guides 112, 212, 312 are configured to guide nails 126, 226, 326 into the fastener holes on the plate 140, 240, 340 during the fixation member impaction process.

Figure 12A:
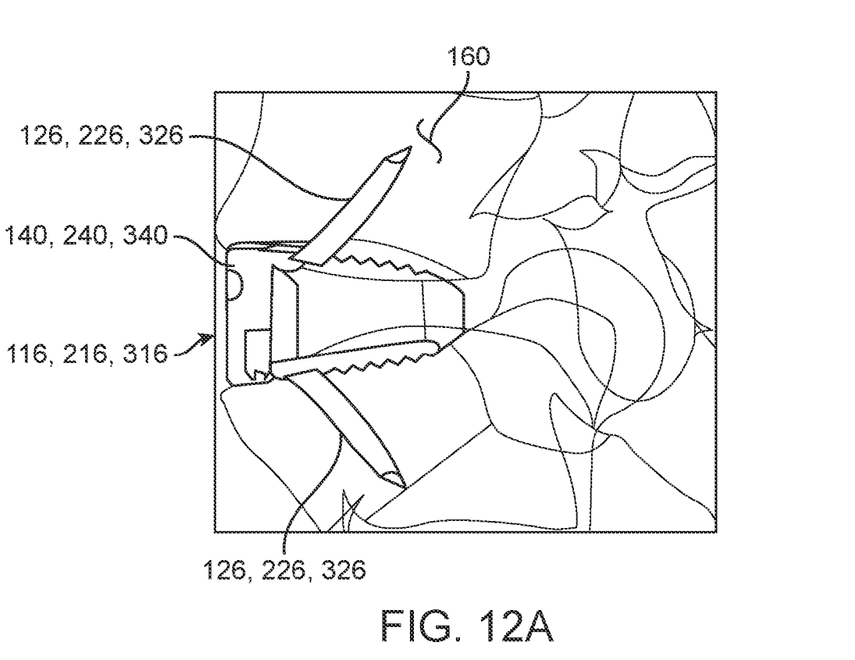
FIG. 12A is a side view and FIG. 12B is a rear view of the interbody spacer positioned between two vertebrae of the spine after deployment of the fixation members into the vertebrae
Figure 12B:
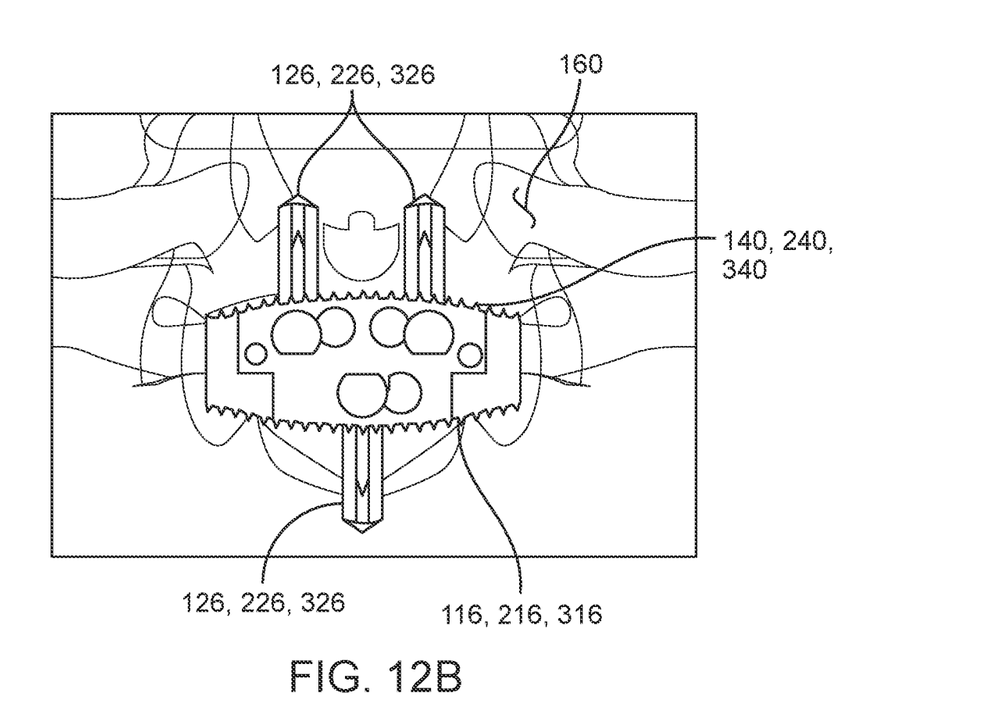

FIG. 12A is a side view and FIG. 12B is a rear view of the interbody spacer 116, 216, 316 positioned between two vertebrae of the spine 160 after deployment of the nails 126, 226, 326 into the vertebrae 160.

Example embodiments of the methods and systems of the present invention have been described herein. As noted elsewhere, these example embodiments have been described for illustrative purposes only and are not limiting. Other embodiments are possible and are covered by the invention. Such embodiments will be apparent to persons skilled in the relevant art(s) based on the teachings contained herein. Thus, the breadth and scope of the present invention should not be limited by any of the above-described exemplary embodiments but should be defined only in accordance with the following claims and their equivalents.

The invention claimed is:

1. An inserter instrument for use with an interbody spacer comprising:
   an inserter body;
   an impaction rod coupled to the inserter body;
   a modular/interchangeable fixation member guide at a distal end of the inserter body having a proximal end contacting the impaction rod and a distal end having two or more deployment prongs contacting two or more fixation members and being configured to simultaneously deliver two or more fixation members to an interbody spacer;
   wherein a fixation member impact end of the impaction rod contacts a proximal impaction end of the fixation member guide deployment rod and is configured to push the two or more fixation member deployment prongs from a proximal position to a distal position to simultaneously deploy two or more fixation members.

2. The inserter instrument of claim 1, wherein two or more fixation member deployment prongs move from a proximal position to a distal position to simultaneously deploy the two or more fixation members.

3. The inserter instrument of claim 1, wherein the modular/interchangeable fixation member guide includes a fixation member guide deployment rod having a proximal end contacting the impaction rod and a distal end having the two or more fixation rod deployment prongs contacting the two or more fixation members.

4. The inserter instrument of claim 1, wherein the modular/interchangeable fixation member guide includes at least two fixation member delivery portals configured to deliver the two or more fixation members to an adjacent spinal vertebrae.

5. The inserter instrument of claim 4, wherein the fixation member delivery portals include an entry hole configured to load the fixation members.

6. The inserter instrument of claim 4, wherein the fixation member delivery portals are curved portals.

7. The inserter instrument of claim 1, wherein the inserter body includes fixation member guide attachment arms on a distal end configured to removably couple with the modular/interchangeable fixation member guide.

8. The inserter instrument of claim 1, wherein the modular/interchangeable fixation member guide is preloaded with two or more fixation members.

9. The inserter instrument of claim 1, wherein the inserter body includes a cannula sized to slidably receive the impaction rod, the impaction rod having an impaction head on a proximal end and a fixation member impact end on a distal end contacting the modular/interchangeable fixation member guide.

10. The inserter instrument of claim 1, wherein the fixation member is selected from the group consisting of: nails, screws, pins, tacks, brads, spikes, cleats, or other suitable fixation members.

11. An inserter instrument for use with an interbody spacer comprising:
an inserter body;
an impaction rod coupled to the inserter body; and
a modular/interchangeable fixation member guide at a distal end of the inserter body contacting the impaction rod, the fixation member guide having two or more deployment prongs at a distal end contacting two or more fixation members;
wherein when a force is applied to the impaction rod, the force is transferred to the two or more deployment prongs being configured to move from a proximal position to a distal position to simultaneously deliver the two or more fixation members to an interbody spacer.

12. The inserter instrument of claim 11, wherein the two or more fixation member deployment prongs contact the two or more fixation members positioned within two or more delivery portals, wherein when a force is applied to the impaction rod the two or more fixation member deployment prongs deploy the two or more fixation members simultaneously.

13. The inserter instrument of claim 11, wherein the inserter body includes a cannula sized to slidably receive the impaction rod, the impaction rod having an impaction head on a proximal end and a fixation member impact end on a distal end coupled to the fixation member guide.

14. The inserter instrument of claim 13, wherein the fixation member is selected from the group consisting of: nails, screws, pins, tacks, brads, spikes, cleats, or other suitable fixation members.

15. An inserter instrument for use with an interbody spacer comprising:
an inserter body;
an impaction rod coupled to the inserter body;
a fixation member guide deployment rod having a proximal end contacting the impaction rod and two or more fixation member deployment prongs at a distal end contacting two or more fixation members, the two or more fixation member deployment prongs being configured to simultaneously deliver two or more fixation members to an interbody spacer;
wherein a fixation member impact end of the impaction rod contacts a proximal impaction end of the fixation member guide deployment rod and is configured to push the two or more fixation member deployment prongs from a proximal position to a distal position to simultaneously deploy two or more fixation members.

16. The inserter instrument of claim 15, further comprising a modular/interchangeable fixation member guide removably coupled to a distal end of the inserter body, the fixation member guide deployment rod being positioned within the modular/interchangeable fixation member guide.

17. The inserter instrument of claim 16, wherein the modular/interchangeable fixation member guide includes at least two fixation member delivery portals configured to deliver the two or more fixation members to an adjacent spinal vertebrae.

18. The inserter instrument of claim 16, wherein the modular/interchangeable fixation member guide is preloaded with two or more fixation members.

* * * * *